US010466177B2

(12) United States Patent
Ge et al.

(10) Patent No.: US 10,466,177 B2
(45) Date of Patent: Nov. 5, 2019

(54) SAMPLE SUBSTANCE MOLECULAR BONDS BREAKDOWN AND SEL COLLECTION

(71) Applicant: Hewlett-Packard Development Company, L.P., Spring, TX (US)

(72) Inventors: Ning Ge, Palo Alto, CA (US); Viktor Shkolnikov, Palo Alto, CA (US); Anita Rogacs, San Diego, CA (US); Paul J. Benning, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/772,493

(22) PCT Filed: Feb. 28, 2016

(86) PCT No.: PCT/US2016/019998
§ 371 (c)(1),
(2) Date: Apr. 30, 2018

(87) PCT Pub. No.: WO2017/146745
PCT Pub. Date: Aug. 31, 2017

(65) Prior Publication Data
US 2019/0079008 A1    Mar. 14, 2019

(51) Int. Cl.
*G01N 21/64* (2006.01)
*G01N 21/65* (2006.01)
*G01N 21/17* (2006.01)

(52) U.S. Cl.
CPC ......... *G01N 21/648* (2013.01); *G01N 21/658* (2013.01); *G01N 2021/1734* (2013.01);
(Continued)

(58) Field of Classification Search
CPC ............... G01N 21/648; G01N 21/658; G01N 2021/1734; G01N 2201/06113; G01N 2201/11
See application file for complete search history.

(56) References Cited

U.S. PATENT DOCUMENTS

| 5,306,403 A | 4/1994 | Vo-Dinh |
| 6,040,191 A * | 3/2000 | Grow ..................... G01N 21/65 436/172 |

(Continued)

FOREIGN PATENT DOCUMENTS

| WO | WO-2012/161683 A1 | 11/2012 |
| WO | WO-2015/116298 A2 | 8/2015 |

OTHER PUBLICATIONS

Tong, Lianming et al.,"Optical Aggregation of Metal Nanoparticles in a Microfluidic Channel for Surface-enhanced Raman Scattering Analysis", The Royal Society of Chemistry 2009, vol. 9, Oct. 27, 2008, p. 193-195 http://icfo.cat/images/publications/J09-002.pdf.

(Continued)

*Primary Examiner* — Dominic J Bologna
(74) *Attorney, Agent, or Firm* — Mannava & Kang

(57) ABSTRACT

A sample comprising a first substance and a second substance is modified by breaking down molecular bonds of the second substance of the sample to form a modified sample having altered surface enhanced luminescence (SEL) characteristics to reduce overlapping of SEL characteristics of the first substance in the second substance. Surface enhanced luminescence data resulting from excitation of the modified sample is collected. Characteristics of the first substance based upon the collected surface enhanced luminescence data are identified.

14 Claims, 3 Drawing Sheets

(52) U.S. Cl.
CPC .............. *G01N 2201/06113* (2013.01); *G01N 2201/11* (2013.01)

(56) References Cited

U.S. PATENT DOCUMENTS

| | | |
|---|---|---|
| 7,659,977 B2 | 2/2010 | Koo |
| 7,982,869 B2 | 7/2011 | Ban et al. |
| 8,129,676 B2 | 3/2012 | Vestel et al. |
| 8,310,671 B1 | 11/2012 | Nguyen et al. |
| 2006/0171656 A1 | 8/2006 | Adachi et al. |
| 2010/0072067 A1 | 3/2010 | Lee et al. |
| 2014/0022531 A1 | 1/2014 | Sackett |
| 2014/0125977 A1 | 5/2014 | Volodin et al. |
| 2014/0350534 A1 | 11/2014 | Kircher et al. |
| 2015/0192590 A1* | 7/2015 | Sodeoka ................ G01N 21/65 435/6.1 |
| 2016/0041101 A1 | 2/2016 | Wackerbarth et al. |
| 2016/0069810 A1* | 3/2016 | Walavalkar .......... G01N 21/658 356/301 |

OTHER PUBLICATIONS

International Search Report and Written Opinion dated Nov. 28, 2016, PCT Patent Application No. PCT/US2016/019998, filed Feb. 28, 2016, Korean Intellectual Property Office.

Bao, Zhi Yong et al. "In situ SERS monitoring of photocatalytic organic decomposition using recyclable Ti02-coated Ag nanowire arrays", Applied Surface Science, vol. 381, Feb. 28, 2814 (2814-82-28), pp. 351-357.

\* cited by examiner

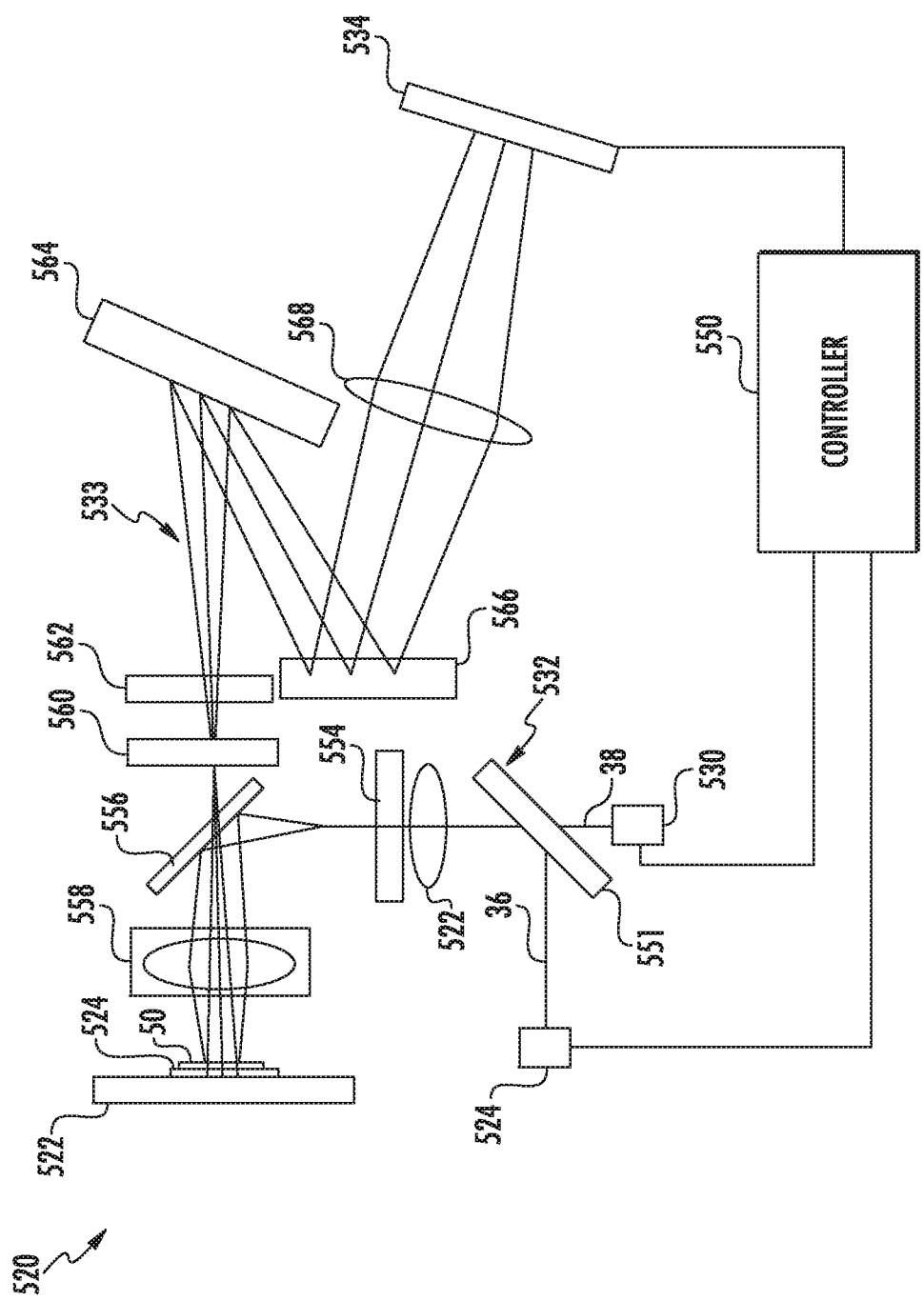

SAMPLE SUBSTANCE MOLECULAR BONDS BREAKDOWN AND SEL COLLECTION

CLAIM FOR PRIORITY

The present application is a national stage filing under 35 U.S.C. § 371 of PCT application number PCT/US2016/019998, having an international filing date of Feb. 28, 2016, the disclosure of which is hereby incorporated by reference in its entirety.

BACKGROUND

Surface enhanced luminescence (SEL) analysis involves the impingement of a sample with photons, such as with a laser beam, and the collection of photo emissions or surface enhanced luminescence. The photo emissions are compared to substance identifying fingerprints to identify the composition of the sample. One example of surface enhanced luminescence analysis is surface enhanced Raman spectroscopy (SERS).

BRIEF DESCRIPTION OF THE DRAWINGS

FIG. 5 is a schematic diagram of an example surface enhanced Ramen spectroscopy analyzer, an example SEL analyzer.

DETAILED DESCRIPTION OF EXAMPLES

Figure 1:
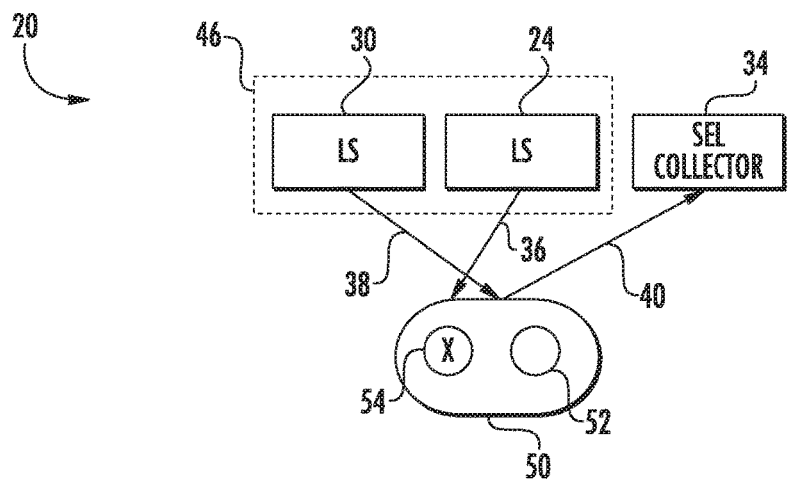
FIG. 1 is a schematic diagram of an example surface enhanced luminescence (SEL) analyzer.

FIG. 1 schematically illustrates an example surface enhanced luminescence (SEL) analyzer 20. SEL analyzer 20 analyzes samples utilizing surface enhanced luminescence. One example of surface enhanced luminescence is surface enhanced Raman spectroscopy (SERS). SEL analysis of a multi-substance sample which has multiple substances is sometimes prone to inaccuracies due to the different substances having overlapping SEL characteristics.

As will be described hereafter, SEL analyzer 20 provides enhanced accuracy for chemical component identification in multi-substance samples. SEL analyzer 20 modifies the sample being analyzed by decomposing at least one substance of the sample by at least breaking down molecular bonds in the at least one substance of the sample. The modified sample has altered SEL characteristics such that SEL characteristics of different substances of the sample do not overlap one another or overlap one another to a lesser extent. As a result, SEL analyzer 20 facilitates more accurate chemical component identification of the multi-substance sample.

As illustrated by FIG. 1, SEL analyzer 20 comprises laser source 24, laser source 30 and SEL collector 34. Laser source 24 comprises a laser having an emission wavelength or a range of emission wavelengths that decomposes a substance of the sample by at least breaking down molecular bonds of a substance of the sample to alter SEL resulting from excitation of the sample by laser source 30. In one implementation, laser source 24 provides a laser beam of photons 36 having a single emission wavelength, wherein the laser beam is focused upon the sample being analyzed. In another implementation, laser source 24 may provide a laser beam of photons 36 having multiple changing emission wavelengths. For example, in one implementation, the laser beam of photons 36 provided by laser source 24 may have emission wavelengths sweeping or scanning across a range of wavelengths. In another implementation, the laser beam of photons 36 provided by laser source 24 may have a plurality of predefined emission wavelengths.

In one implementation, laser source 24 comprises an ultraviolet laser source. In one implementation, laser source 24 has an emission wavelength of 40 nm to 400 nm. In one implementation, laser source 24 outputs a laser beam having a wavelength of 254 nm. In other implementations, laser source 24 may output a laser beam having other wavelengths.

In one implementation, laser source 24 is to direct a laser beam of photons 36 at the sample being analyzed with a selected wavelength or group of wavelengths for a predetermined duration or dose so as to break down molecular bonds of a non-target substance of the sample which may have SEL characteristics that overlap SEL characteristics of a target substance. The selected wavelength or group of wavelengths and the predetermined duration or dose are such that the molecular bonds of the target substance are not broken down and do not have altered SEL characteristics. In one implementation, the wavelength and dose of laser beam 36 breaks down the molecular bonds of a majority, and in some implementations all, of the non-target substance while not vaporizing the non-target substance. In one implementation, laser source 24 directs a laser beam 36 of photons having a wavelength and for a sufficient duration or dose so as to leave the non-target substance with the broken molecular bonds as part of the sample without vaporization/ablation of a majority of the non-target substance. As a result, the underlying SEL structure supporting the sample may remain at least substantially intact. In yet other implementations, laser source 24 directs a laser beam of photons 36 having a wavelength or group of wavelengths and for a predetermined duration/dose so as to vaporize or ablate a majority of the non-target substance. In one implementation laser source 24 directs the laser beam of photons 36 of photons having a wavelength or group of wavelengths and for predetermined duration so as to completely vaporize and remove the non-target substance.

Laser source 30 comprises a source of photons 38 that have wavelengths selected to excite the sample such that the sample emits photons 40 which are collected and sensed by SEL collector 34. In one implementation laser 30 outputs photons 38 in the form of a laser beam focused upon the sample being analyzed. In other implementations, depending upon the sample and its underlying support, photons 38 may be applied in forms other than a laser beam.

In implementation, laser source 30 has an emission wavelength that excites the sample to a state of surface enhanced luminescence. In one implementation, laser source 30 has an emission wavelength of between 500 and 900 nm. In one implementation, laser source 30 has a wavelength of a visible light. In one particular implementation, laser source 30 has a wavelength of 785 nm. In another implementation, laser source 30 has a wavelength of 687 nm. In yet other implementations, laser 30 may have other emission wavelengths depending upon the target substance of the sample being analyzed and the characteristics of the substrate or stage supporting the sample.

In the example illustrated, laser source 24 and laser source 30 comprise distinct lasers or laser emitting devices. In one implementation, laser source 24 and laser source 30 share optical directing and focusing elements. For example, in one implementation, laser source 24 and laser source 30 share lenses and mirrors which adjusts the laser beams and direct the laser beams from sources 24 and 30 towards the sample. As a result, analyzer 20 may be less expensive and may be more compact. In other implementations, as indicated by broken lines 46, laser source 24 and laser source 30 may be provided by a single laser device that is selectively controllable or adjustable so as to serve as a source for both photons 36 and photons 38. In one implementation, laser source 24, laser source 30 and SEL collector 34 are provided as a single unit.

SEL collector 34 comprises a device that collects and senses photons 40 emanating from the sample being analyzed. In one implementation, SEL collector 34 comprises a photomultiplier. In one implementation, SEL collector 34 comprises a charge coupled device (CCD), an electron multiplying charge coupled device (EMCCD), a complementary metal-oxide semi-conductor (CMOS) device or a photomultiplier tube (PMT). As described hereafter, in some implementations, additional optical components may be provided to focus, direct or alter the photons 40 being emanating from the sample prior to the photons 40 being received by collector 34. For example, such optical components may comprise notch or edge filters, mirrors, or focusing lenses.

Figure 2:
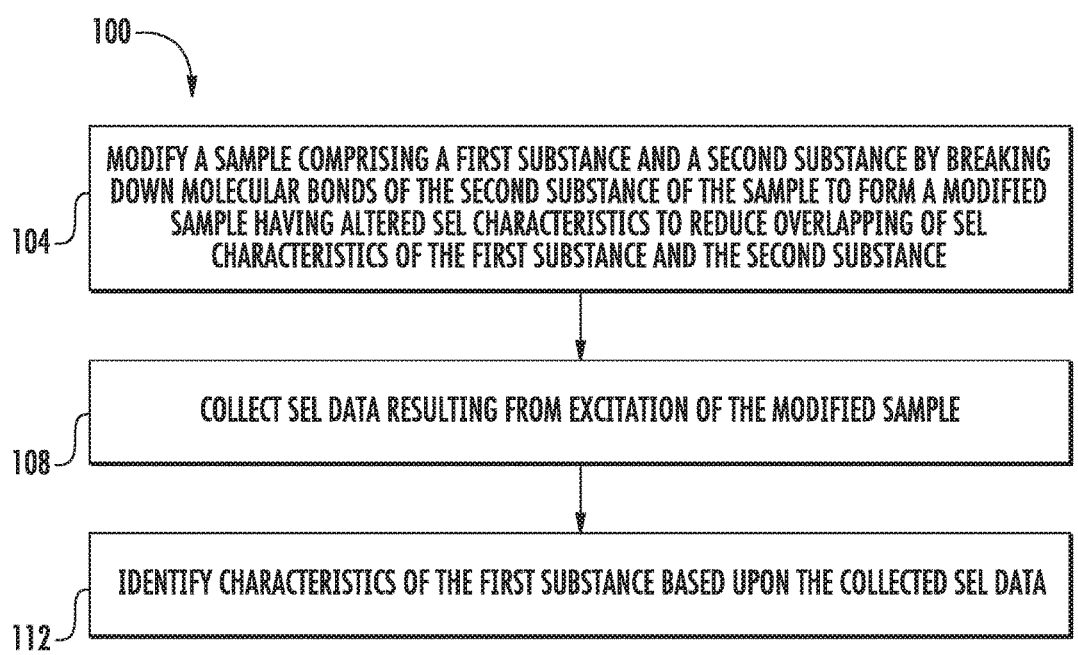
FIG. 2 is a flow diagram of an example method for analyzing a substance using SEL.

FIG. 2 is a flow diagram illustrating an example method 100 for analyzing a sample using surface enhanced luminescence. For purposes of description, method 100 is described as being carried out by analyzer 20 as illustrated in FIG. 1. Method 100 may alternatively be carried out by any of the analyzers described hereafter or other appropriately designed analyzers.

As indicated by block 104 of method 100, a sample comprising a first substance and a second substance is modified by breaking down molecular bonds of the second substance of the sample to form a modified sample. The modified sample has altered SEL characteristics that reduce overlapping of SEL characteristics of the first substance and the second substance.

As illustrated by the example in FIG. 1, an example sample 50 (schematically illustrated) having a target substance 52 (schematically illustrated) and a non-target substance 54 (schematically illustrated) is presented to analyzer 20 to carry out method 100. In one implementation, the sample 50 is presented upon a SEL structure that further enhances or facilitates the emission of SEL from the sample upon being excited by photons 38. For example, in one implementation in which analyzer 20 comprises a Raman spectroscopy analyzer, sample 50 may be supported upon a surface enhanced Raman spectroscopy (SERS) structure. In yet other implementations, sample 50 may be supported upon a SEL structure that facilitates other forms of SEL analysis.

Substances 52 and 54 may be of a nature such that they, when their molecular bonds are intact, have SEL characteristics which may overlap one another. In other words, in the absence of being modified pursuant to block 104 and when excited by photons 38, substances 52 and 54 have chemical compositions such that they emit photons 40 that have similar or the same characteristics, impairing the ability of surface enhanced luminescence analysis to aptly distinguish between substances 52 and 54 and to identify characteristics of the target substance 52.

To enhance the ability of SEL collector 34 to aptly distinguish between substances 52 and 54 and to identify characteristics of the target substance 52, laser source 24 carries out the modification described in block 104 by directing photons 36 at sample 50. The photons 36 provided by laser source 24 break down the molecular bonds of substance 54 (as schematically indicated by the "X") while not breaking down the molecular bonds of the target substance 52 or breaking down the molecular bonds of target substance 52 so as to not impair or substantially change the SEL characteristics of the target substance 52. As schematically shown by 1, photons 36 are broadly directed across a substantial portion of the sample 50, if not all of the sample 50, impinging both substances 52 and 54.

In one implementation, laser source 24 directs a laser beam of photons 36 having a wavelength and for a sufficient duration so as to leave the non-target substance 54 with the broken molecular bonds as part of the sample without vaporization/ablation of a majority of the substance. As a result, the underlying SEL stage or structure supporting the sample may remain at least substantially intact. In yet other implementations, laser source 24 directs a laser beam of photons 36 having a wavelength or group of wavelengths and for a predetermined duration so as to break down molecular bonds, but also vaporize or ablate a majority of the non-target substance. In one implementation laser source 24 directs the laser beam of photons 36 having a wavelength or group of wavelengths and for predetermined duration so as to completely vaporize and remove the non-target substance 54. In one example, sample 50 is impinged by ultraviolet electromagnetic radiation from laser source 24 that breaks down the molecular bonds. In other implementations, sample 50 may be impinged by electromagnetic radiation from the source 24 having other wavelengths.

As indicated by block 108 of FIG. 2, SEL collector 34 collects SEL data resulting from excitation of the modified sample. As shown by 1, excitation of sample 50 results in the emission of photons 40 which are possibly filtered and/or amplified and directed to collector 34. Collector 34, a sensor, outputs signals which vary depending upon the characteristics of photons 40.

As indicated by block 112, the signals output by collector 34 are then used to identify characteristics of the target substance 52. The collected SEL data is used to identify the characteristics of the target substance 52. In one implementation, the collected SEL date is compared to historical SEL data associated with chemicals or chemical compositions (the SEL fingerprints of chemicals or chemical compositions) to identify the chemical composition of the target substance 52 and/are the composition of sample 50. In some implementations, the characteristics of the non-target substance 54 may also be identified or estimated based upon the characteristics of photons 36 and changes in the SEL characteristics or properties of the sample 50 resulting from the application of photons 36.

Figure 3:
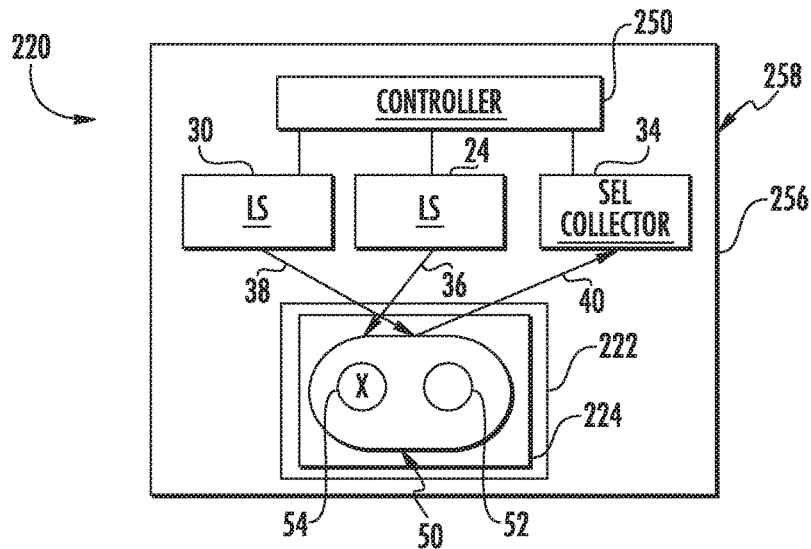
FIG. 3 is a schematic diagram of an example SEL analyzer.

FIG. 3 schematically illustrates SEL analyzer 220, an example implementation of SEL analyzer 20. SEL analyzer 220 is similar to SEL analyzer 20 except that SEL analyzer 220 is additionally illustrated as comprising analyzer stage 222 and controller 250. Analyzer stage 222 comprises a structure that removably or releasably supports sample 50 when being analyzed. In the example illustrated, analyzer stage 222 comprises structure that releasably and/or removably supports a SEL structure 224 upon which sample 50 is provided. For purposes of this disclosure, the term "releasably" or "removably" with respect to an attachment or coupling of two structures means that the two structures may be repeatedly connected and disconnected to and from one another without material damage to either of the two structures or their functioning. In the example illustrated, stage 222 allows sample 50 and the underlying SEL structure 224 to be separated from analyzer 220, facilitating the use of analyzer 220 on multiple different samples and their underlying SEL structures 224.

SEL structure 224 enhances or facilitates the emission of SEL from the sample upon being excited by photons 38. SEL structure 224 comprises enhanced fluorescence spectroscopy structures or enhanced luminescence spectroscopy structures. For example, in one implementation, SEL structure 224 may comprise SEL particles. Examples of SEL particles include, but are not limited to, electrodes in electrolytic cells and metal colloid solutions.

In one implementation in which analyzer 20 comprises a Raman spectroscopy analyzer, structure 224 may comprise a surface enhanced Raman spectroscopy (SERS) structure. In such an implementation, structure 224 may include a metal surface or structure, wherein interactions between the analyte and the metal surface cause an increase in the intensity of the Raman-scattered radiation. Such metal surfaces may include a roughened metal surface, such as periodic gratings. In another implementation, such metal surfaces may comprise assembled nanoparticles. In some implementations, such metal surfaces may comprise metal islands. In one implementation, such metal islands comprise flexible columnar supports such as pillars, needles, fingers, particles or wires. In some implementations, the flexible columnar structures may include a metal cap or head upon which an analyte may be deposited. In some implementations, such columnar structures are formed from materials and/or are dimensioned so as to bend or flex towards and away from one another in response to applied electric fields. In some implementations, the SERS structures are movable and are self-actuating, wherein such columnar structures bend or flex towards one another in response to microcapillary forces so as to self-organize, wherein such bending facilitates close spacing between the structures for greater scattered radiation intensity.

In some implementations, the columnar structures are electrically conductive such that the columnar structures and/or their metal caps or heads provide distinct charging points intensifying the generated electric field at distinct points to enhance attraction of the charged ions of the analyte to the columnar structures of structure 224. For example, in some implementations, the columnar structures are formed from an electrically conductive polymer such as Poly(3,4-ethylenedioxythiophene) or PEDOT (or sometimes PEDT), a conducting polymer based on 3,4-ethylenedioxythiophene or EDOT monomer. In one implementation, the SERS structures have a nanometer scale to facilitate nano-enhanced Raman spectroscopy (NERS). Such nano-scale NERS structures may increase the intensity of radiation scattered by the analyte adsorbed on such structures by a factor as high $10^{10}$ or even as high as $10^{16}$. In yet other implementations, such columnar structures may be formed from non-electrically conductive materials, such as non-electrically conductive polymers, or may be formed from metal materials, such as wire filaments or the like.

In the example illustrated, analyzer stage 222 is fixedly coupled to laser source 24, laser source 30 and collector 24 by a single frame or framework 256 providing a single self-contained unit 258. For purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. In the example illustrated, analyzer stage 222 is further physically coupled to controller 250 as a single unit. In other implementations, controller 250 may be an independent unit that is connected to or plugged into the unit 258.

Controller 250 comprises a processing unit that follows instructions in controlling at least the operation of laser source 24, laser source 30 and SEL collector 34. For purposes of this application, the term "processing unit" shall mean electronics or computing hardware that executes sequences of instructions contained in a non-transitory memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 250 may be embodied as part of one or more application-specific integrated circuits (ASICs). Unless otherwise specifically noted, the controller is not limited to any specific combination of hardware circuitry and software, nor to any particular source for the instructions executed by the processing unit.

Figure 4:
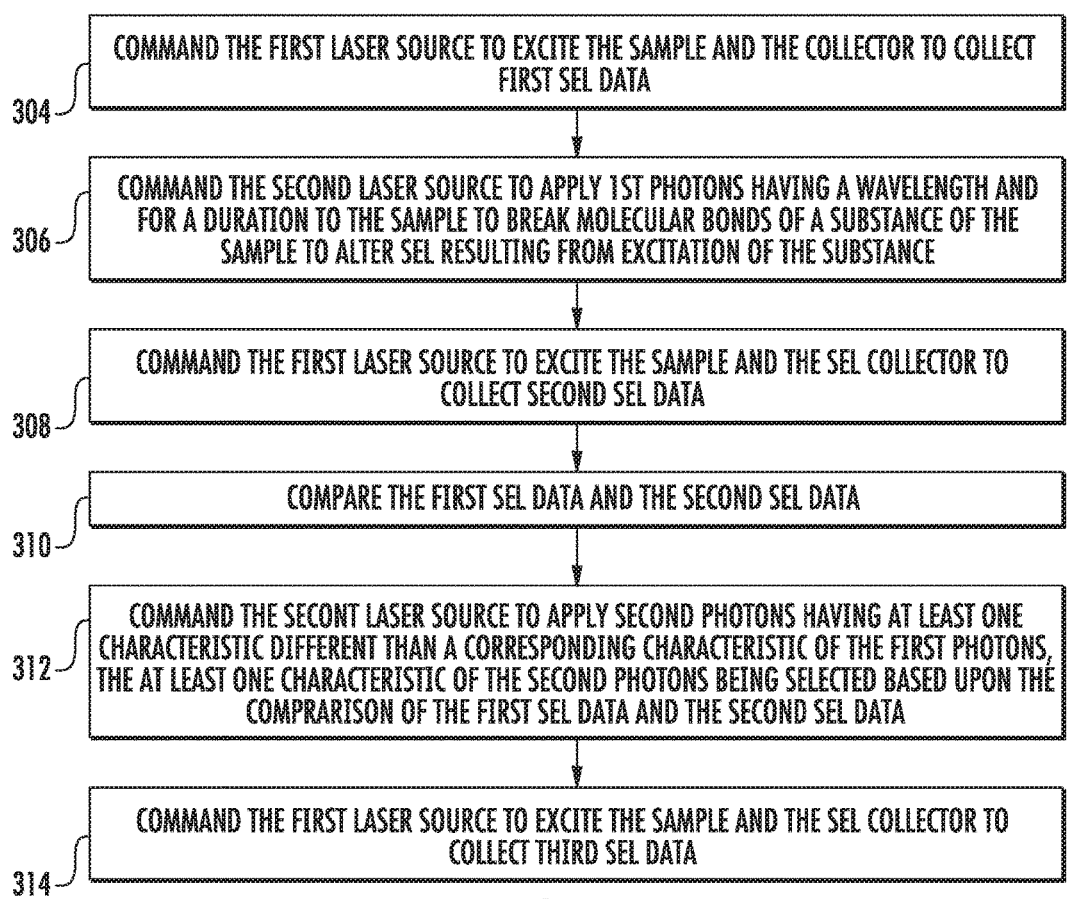
FIG. 4 is a flow diagram of an example method for analyzing substance using SEL.

In the example illustrated, controller 250, following instructions contained in a non-transitory memory, carries out the example method 300 illustrated in FIG. 4 for testing are analyzing a sample. As indicated by block 304 of FIG. 4, controller 250, following the instructions contained in the non-transitory memory, commands laser source 30 to excite sample 50 by impinging sample 50 with photons 38. In the example illustrated, photons 38 are transmitted in the form of a laser beam. As further indicated by block 304, controller 250 commands collector 34 to collect initial or first SEL data, wherein the data is based upon the photons 40 emitted by sample 50 (and possibly the underlying structure 224) in response to being excited by photons 38.

As indicated by block 306, after receipt of the initial SEL data, controller 250 commands laser source 24 to apply first photons 36 to sample 50. In one implementation, the first photons 36 are applied in the form of a laser beam. The first photons 36 are applied for a duration/dose and have an emission wavelength that results in molecular bonds of the non-target substance 54 being broken. In one implementation, the duration and wavelength of the first photons breaks the molecular bonds of the non-target substance 54 without vaporizing/ablating any or at least a majority of the non-target substance 54. In another implementation, the duration and emission wavelength of the first photons is sufficient to not only break the molecular bonds, but vaporize portions or a majority of the non-target substance 54. The duration and the wavelength of the first photons do not decompose and do not break the molecular bonds of the target substance 52. Because the bonds of the non-target substance 54 are broken, the contribution of photons 40 from the non-target substance 54 is altered or reduced such that any overlap between the SEL from the non-target substance 54 and the target substance 52 is at least reduced.

As indicated by block 308, after application of the first photons 36, controller 250 commands laser source 32 once again excite the now modified sample 50 by impinging the now modified sample 50 once again with photons 38. In the example illustrated, photons 38 are transmitted in the form of a laser beam. As further indicated by block 308, controller 250 commands collector 34 to collect follow-up or second SEL data, wherein the data is based upon the photons 40 emitted by the modified sample 50 (and possibly the underlying structure 224) in response to being excited by photons 38. As a result of the prior modification of sample 50 in block 306, the second SEL data may be different than the first SEL data.

As indicated by block 310, controller 250, following the instructions contained in the non-transitory memory, compares the first SEL data and the second SEL data.

As indicated by block 312, controller 250 commands laser source 24 to apply second photons 36 to sample 50. In one implementation, the second photons 36 are applied in the form of a laser beam. The second photons 36 have at least one characteristic (other than impingement location) different than a corresponding characteristic of the previously applied first photons 36. Controller 250 determines or selects the value or values for the at least one characteristic of the second photons based upon the prior comparison of the first SEL data and the second SEL data in block 310. As a result, method 300 involves close loop feedback to adjust repeated applications of photons 36 to sample 50 to enhance the reduction or elimination of overlapping SEL characteristics of different substances of sample 50.

In one implementation, the at least one characteristic of the second photons applied to sample 50 is the wavelength of the second photons, wherein the wavelength of the second photons is different than the wavelength of the prior applied first photons. In yet another implementation, the at least one characteristic of the second photons is the duration during which the second photons are applied to sample 50. In one implementation, controller 250 adjusts both the wavelength and the application duration of the second photons 36 based upon the comparison of the first SEL data and the second SEL data.

As with application of the first photons in block 306, the application of the second photons in block 312 is for a duration and with a wavelength that results in additional remaining molecular bonds of the non-target substance 54 being broken and/or the molecular bonds of other non-target substances being broken to alter their SEL characteristics and reduce their overlap with the SEL characteristics of the target substance 52. For example, the comparison of the first SEL data and the second SEL data may indicate that the molecular bonds of the non-target substance 54 have not been satisfactorily broken but for not all of the molecular bonds have been broken) with the prior wavelength and/or duration of the application of first photons. Controller 250 may adjust the application duration and/or wavelength of the second photons to more completely break the molecular bonds of the non-target substance 54 for enhanced performance by analyzer 220. By way of another example, the comparison of the first SEL data and the second SEL data may indicate additional non-target substances or additional overlapping SEL characteristics from other non-target substances that should be altered. Controller 250 may adjust the application duration and such are wavelength of the second photons to break the molecular bonds of the additional non-target substances in the sample 50.

In one implementation, the duration and wavelength of the second photons breaks the molecular bonds of the non-target substance 54 without vaporizing/ablating any or at least a majority of the non-target substance 54. In another implementation, the duration and emission wavelength of the second photons is sufficient to not only break the molecular bonds, but vaporize portions or a majority of the non-target substance 54. The duration and the wavelength of the second photons do not decompose and do not break the molecular bonds of the target substance 52. Because the bonds of the non-target substance 54 are broken, the contribution of photons 40 from the non-target substance 54 is altered or reduced such that any overlap between the SEL from the non-target substance 54 (and any additional non-target substances for which the molecular bonds are broken by the second photons) and the target substance 52 is at least reduced.

As indicated by block 314, controller 250 commands collector 34 to collect third SEL data, wherein the third SEL data is based upon the photons 40 emitted by the further modified sample 50 (and possibly the underlying structure 224) in response to being excited by photons 38. As a result of the prior modification of sample 50 in block 306, the third SEL data may be different than the second SEL data, wherein the third SEL data may have less overlapping SEL characteristics to better facilitate distinguishing portions of the SEL data originating from the target substance 52 with respect to portions of the SEL data originating from other non-target substances in sample 50. As a result, method 300 facilitates accurate and reliable identification of substance 52 and/or its characteristics.

In one example implementation, method 100 or method 300 may be applied to a sample containing two individual chemical compounds that sometimes appear together, such as melamine, sometimes a target substance and 1,1'-Azobis (cyclohexanecarbonitrile). In many circumstances, the melamine and 1,1'-Azobis(cyclohexanecarbonitrile) may have overlapping Raman peaks at 150, 650 and 1000 $cm^{-1}$. As a result, each of the compounds will mask the signal of the other.

In the example implementation, method 100 or method 200 may be carried out by system 20 or system 220 upon a sample containing both 1,1'-Azobis(cyclohexanecarbonitrile) and melamine to enhance the accuracy of such chemical compound identification. In one implementation, when analyzing such an example sample, latest source 24 is directed to apply an ultraviolet laser beam on the sample. The UV laser beam is applied for a duration of 10-100 ms (10-100 mJ) to form a modified sample. As a result, the non-target substance or compound 1,1'-Azobis(cyclohexanecarbonitrile) is decomposed, wherein the molecular bonds are broken down to change the SERS spectrum of the 1,1'-Azobis(cyclohexanecarbonitrile) compound. In the example illustrated, the Raman spectra peaks (the SEL or SERS characteristics) which occur at 150, 650 and 1000 cm-1 are reduced or eliminated. As melamine is more robust, the UV laser beam applied to the sample does not break down a sufficient number of molecular bonds of the melamine to alter its SERS spectrum or its Raman peaks at 150, 650 and 1000 cm-1. Because the overlapping Raman peaks of the non-target substance or compound are reduced or eliminated while the corresponding peaks of the target substance or compound survive, methods 100 and 300 provide enhanced identification of the Raman spectra peaks of the target substance, melamine. As a result, the SERS data collected by collector 34 from the modified sample of melamine and 1,1'-Azobis(cyclohexanecarbonitrile) may better distinguish between melamine and the nontarget compound, facilitating more accurate chemical component application.

Analyzers 20 and 220 as well as methods 100 and 300 may be applied to many other samples having different concurrently occurring substances. For example, other non-target substances or chemical compositions that may decompose under UV light, such as a light having a wavelength of 254 nm, include, but are not limited to, Azobisisobutyronitrile; 4,4'-Azobis(4-cyanovaleric acid); 2,2'-Azobis(2-methylpropionamidine) dihydrochloride, and benzoin methyl ether. In other implementations, the wavelength and/or duration of the photons applied by laser source 24 may be adjusted to break the molecular bonds of other non-target substances or compounds prior to excitation of the modified sample for SEL data collection and analysis.

FIG. 5 is a diagram schematically illustrating SEL analyzer 520, an example implementation of analyzer 20 or analyzer 220. In the example illustrated, SEL analyzer 520 comprises an SERS analyzer which may carry out method 100 or method 300 described above. Analyzer 520 comprises stage 522, laser source 524, laser source 530, laser directing optics 532, SERS spectra optics 533, SERS collector 534 and controller 550.

Stage 522 removably or releasably supports an SERS structure 524 upon which the sample 50 (schematically illustrated) is presented. Laser source 524 and laser source 530 are similar to laser source 24 and laser source 30 described above. In the example illustrated, laser sources 524 and 530 comprise separate and independent laser sources, wherein both of such laser sources direct laser beams to the structure 524 and sample 50 supported by stage 522 using a shared set of laser directing optics 532.

Laser directing optics 532 direct, at different times, photons 36 and photons 38 to SERS structure 524 on stage 522. In the example illustrated, optics 532 comprise beam splitter 551, beam expander 552, laser filter 554, dichroic mirror 556 and focusing lens 558. Beams splitter 551 facilitates the sharing of beam expander 552, laser filter 554, dichroic mirror 556 and focusing lens 558 by each of laser sources 524 and 530. Beam expander 552 expands laser beams received from either of laser sources 524, 530 while filter 554 reduces or eliminates unwanted laser background, scatter and plasma to optimize signal-to-noise. Although schematically illustrated as a single filter 554, filter 554 may comprise multiple separate consecutive filters. Dichroic mirror 556 redirects laser beams towards focusing lens 558. Focusing lens 558 focuses the individual laser beams from laser sources 524 and 530 onto the sample 50 and SERS structure 524. In other implementations, laser directing optics 532 may comprise additional or fewer of such optical components depending upon characteristics of the laser beam provided by each of laser sources 524, 530 and the path for such laser beams to reach SERS structure 524 and stage 522.

SERS spectra optics 533 correct SERS spectra, photoluminescence or SEL emitted by sample 50 towards collector 534. Optics 533 may focus, focus or amplify the SEL prior to the SEL reaching collector 534. In the example illustrated, optics 533 comprises focusing lens 558, dichroic mirror 556 (each of which is described above), laser filter 560, grating lens 562, mirror 564, mirror 566 and focusing lens 568. Focusing lens 558 captures the photons emitted by the excited sample 50 and passes focused photons through dichroic mirror 566 and through laser filter 560 and grating lens 562 onto mirror 564. Laser filter 560, similar to laser filter 554, reduces or eliminates unwanted laser background, scatter and plasma to optimize signal-to-noise. Grating lens 562 spreads the captured photons prior to directing the captured photons onto mirror 564. Mirrors 564 and 566 redirect the light while continuing to expand the photons or light prior to the light being captured and focused by focusing lens 568 onto collector 534.

Collector 534 is similar to collector 34 described above. Collector 534 outputs signals indicating spectra of the captured photons. Examples of such spectra for one example sample are shown in FIGS. 5 and 6. As described above, such spectra may be compared to spectra fingerprints to identify chemical compositions of sample 50. In other implementations, SERS spectra optics 533 may have additional or fewer components and may have alternative arrangements depending upon the properties of the photons emitted from sample 50 upon being excited as well the path for such photons from stage 522 to collector 534.

Controller 550 is similar to controller 250 described above. Controller 550 comprises a processing unit that follows instructions in a non-transitory computer-readable medium or memory to carry out method 100 and/or method 300 described above. Controller 550 modifies a sample 50 on SERS structure 524 and stage 522 by breaking down molecular bonds of non-target compounds or substances while leaving the targeted compounds or substances unaltered. In one implementation, the laser beam applied by laser source 524 breaks down the molecular bonds of the non-target compounds or substances without substantially damaging or altering the molecular bonds of the target substances or compounds and without damaging or altering the underlying STRS structure 524. "Substantial" damage to the molecular bonds of the target substance means that the SEL or Raman spectra having altered characteristics so as to no longer be matchable to the fingerprint SEL or Raman spectra for identifying chemical compounds. Overlapping Raman spectra of non-target compounds or substances are reduced or eliminated. As a result, controller 550 has enhanced accuracy with respect to identifying characteristics of the target compound or substrate utilizing the collected data from collector 534.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims mirrorly distinguish different elements and, unless otherwise stated, are not to be specifically associated with a particular order or particular numbering of elements in the disclosure.

What is claimed is:
1. An apparatus comprising:
   a first laser source to output a first light having a first emission wavelength; and
   a second laser source to output a second light having a second emission wavelength, the second emission wavelength being lower than the first emission wavelength;

a surface enhanced luminescence (SEL) collector to collect SEL resulting from application of the first light from the first laser source onto a sample; and a controller to:
command the first laser source to apply the first light onto the sample;
receive first SEL data from the SEL collector resulting from the application of the first light onto the sample;
after receipt of the first SEL data, command the second laser source to apply first photons having the second emission wavelength to the sample to break molecular bonds of a substance of the sample to alter SEL resulting from excitation of the substance;
after the application of the first photons having the second emission wavelength to the sample, command the first laser source to re-apply the first light onto the sample; and
receive second SEL data from the SEL collector resulting from the re-application of the first light onto the sample; and
compare the first SEL data and the second SEL data.

2. The apparatus of claim 1, wherein the second laser source is to apply the first photons having the second emission wavelength and at a certain dose to leave the substance in the sample with the broken molecular bonds as part of the sample without vaporization of a majority of the substance.

3. The apparatus of claim 1, wherein the second laser source is to apply the first photons at the second emission wavelength to vaporize a majority of the substance in the sample.

4. The apparatus of claim 1, wherein the controller is further to command the second laser source to apply the first photons to have wavelengths that sweep across a range of emission wavelengths including the second emission wavelength.

5. The apparatus of claim 1, wherein the controller is further to:
command the second laser source to apply second photons having at least one characteristic different than a corresponding characteristic of the first photons, the at least one characteristic of the second photons that is different than the corresponding characteristic of the first photons being selected based upon the comparison of the first SEL data and the second SEL data;
after the application of the second photons, command the first laser source to further apply the first light onto the sample; and
receive third SEL data from the SEL collector.

6. The apparatus of claim 5, wherein the at least one characteristic of the second photons is selected to further breakdown molecular bonds of the substance of the sample to further alter SEL resulting from excitation of the sample.

7. The apparatus of claim 5, wherein the at least one characteristic of the second photons is selected to breakdown molecular bonds of a second substance, different than the first substance, of the sample.

8. The apparatus of claim 5, wherein the at least one characteristic of the second photons is selected from a group of characteristics consisting of photon wavelength and photon application duration.

9. The apparatus of claim 1, wherein the SEL collector comprises a Raman collector to collect Raman scattering resulting from excitation of the sample.

10. The apparatus of claim 1, wherein the first laser source is a visible laser source and wherein the second laser source is an ultraviolet laser source.

11. The apparatus of claim 1, further comprising a support coupled to the first laser source and the second laser source to position a substrate on which the sample is to be retained with respect to the first laser source and the second laser source.

12. A method comprising:
modifying a sample comprising a first substance and a second substance by breaking down molecular bonds of the second substance of the sample to form a modified sample having altered surface enhanced luminescence (SEL) characteristics to reduce overlapping of SEL characteristics of the first substance and the second substance;
collecting surface enhanced luminescence data resulting from excitation of the modified sample; and
identifying characteristics of the first substance based upon the collected surface enhanced luminescence data.

13. The method of claim 12, wherein the SEL data comprise Raman spectra peaks and wherein the molecular bonds of the second substance are broken down to remove Raman spectra peaks of the second substance that overlap Raman spectra peaks of the first substance.

14. A non-transitory computer-readable medium comprising instructions to direct a processing unit to:
output control signals to command a first laser source to output first photons at a first emission wavelength onto a sample to excite the sample to a state of surface enhanced luminescence (SEL);
output control signals to command a SEL collector to collect a first SEL resulting from the application of the first photons onto the sample;
output control signals to command a second laser source to output second photons at a second emission wavelength onto the sample, the second emission wavelength being lower than the first emission wavelength, wherein the second photons are to break molecular bonds of a substance of the sample to alter SEL resulting from excitation of the sample;
output control signals to command the first laser source to output third photons onto the sample to excite the sample to a state of SEL;
output control signals to command the SEL collector to collect a second SEL resulting from the application of the third photons onto the sample; and
compare the first SEL and the second SEL.

* * * * *